United States Patent [19]
Stiefel et al.

[11] Patent Number: 5,888,945
[45] Date of Patent: Mar. 30, 1999

[54] METHOD FOR ENHANCING AND RESTORING REDUCTION FRICTION EFFECTIVENESS

[75] Inventors: Edward Ira Stiefel, Bridgewater; Jonathan M. McConnachie; Daniel Paul Leta, both of Flemington, all of N.J.

[73] Assignee: Exxon Research and Engineering Company, Florham Park, N.J.

[21] Appl. No.: 766,830

[22] Filed: Dec. 13, 1996

[51] Int. Cl.⁶ .................................................. C10M 139/00
[52] U.S. Cl. ............................. 508/363; 508/367; 508/370
[58] Field of Search .................... 508/363, 362, 508/367, 370

[56] References Cited

U.S. PATENT DOCUMENTS

| | | | |
|---|---|---|---|
| 4,705,641 | 11/1987 | Goldblatt et al. | 252/35 |
| 4,846,983 | 7/1989 | Ward, Jr. | 508/363 |
| 4,867,890 | 9/1989 | Colclough et al. | 508/373 |
| 4,966,719 | 10/1990 | Coyle et al. | 252/42.7 |
| 4,978,464 | 12/1990 | Coyle et al. | 252/42.7 |
| 4,995,996 | 2/1991 | Coyle et al. | 252/42.7 |

FOREIGN PATENT DOCUMENTS

95/19411  7/1995  WIPO .

OTHER PUBLICATIONS

Syntheses of Sulphur–Bridged Molybdenum and Tungsten Coordination Compounds, Takashi Shibahara, pp. 73–147; Dept. of Chemistry, Okayama University of Science; Japan; Rec'd. May 20, 1992.

*Primary Examiner*—Jerry D. Johnson
*Attorney, Agent, or Firm*—Gerard J. Hugh

[57] ABSTRACT

The invention is a method for enhancing and restoring the friction reduction effectiveness of a lubricating oil comprising adding to the lubricating oil a trinuclear molybdenum sulfur compound selected from the group of trinuclear molybdenum compounds preferably those having the formulas $Mo_3S_7(dtc)_4$ and $Mo_3S_4(dtc)_4$ and mixtures thereof wherein dtc represents independently selected diorganodithiocarbamate ligands containing independently selected organo groups and wherein the ligands have a sufficient number of carbon atoms among all the organo groups of the compound's ligands are present to render the compound soluble or dispersible in the lubricating oil. The oil may be a fresh or used oil. Concentrates of the composition are also included in the invention.

11 Claims, 4 Drawing Sheets

METHOD FOR ENHANCING AND RESTORING REDUCTION FRICTION EFFECTIVENESS

FIELD OF THE INVENTION

The present invention relates to a method for the enhancement and restoration of friction reducing properties in a lubricating composition.

BACKGROUND OF THE INVENTION

Molybdenum disulfide is a well known lubricant. Unfortunately, its use as an additive in oils of lubricating viscosity is limited by its insolubility in oil. Consequently, oil-soluble molybdenum sulfur-containing compounds have been proposed and investigated for use as lubricating oil additives.

Commercially available dinuclear molybdenum sulfide lubricating oil additives are well known in the art. For example, the composition $Mo_2O_2S_2(dtc)_2$ can be added to a fresh oil of lubricating viscosity in order to enhance the oil's friction reducing properties. In the formula $Mo_2O_2S_2(dtc)_2$, dtc represents diorganodithiocarbamate ligands that are connected to the dinuclear molybdenum sulfide core.

As is known in the art, lubricating oil compositions containing molybdenum sulfide additives lose their friction reducing effectiveness over time when used in an internal combustion engine. While an enhancement in friction reducing properties is observed when the compound is added to a fresh oil, little if any friction reduction is observed when $Mo_2O_2S_2(dtc)_2$ is added to a used oil in which a loss in friction reducing properties has occurred, depending on the degree of oil aging and degradation.

Consequently, there remains a need for a composition that is capable of enhancing and restoring the friction reducing effectiveness of lubricating oils.

SUMMARY OF THE INVENTION

Figure 1:
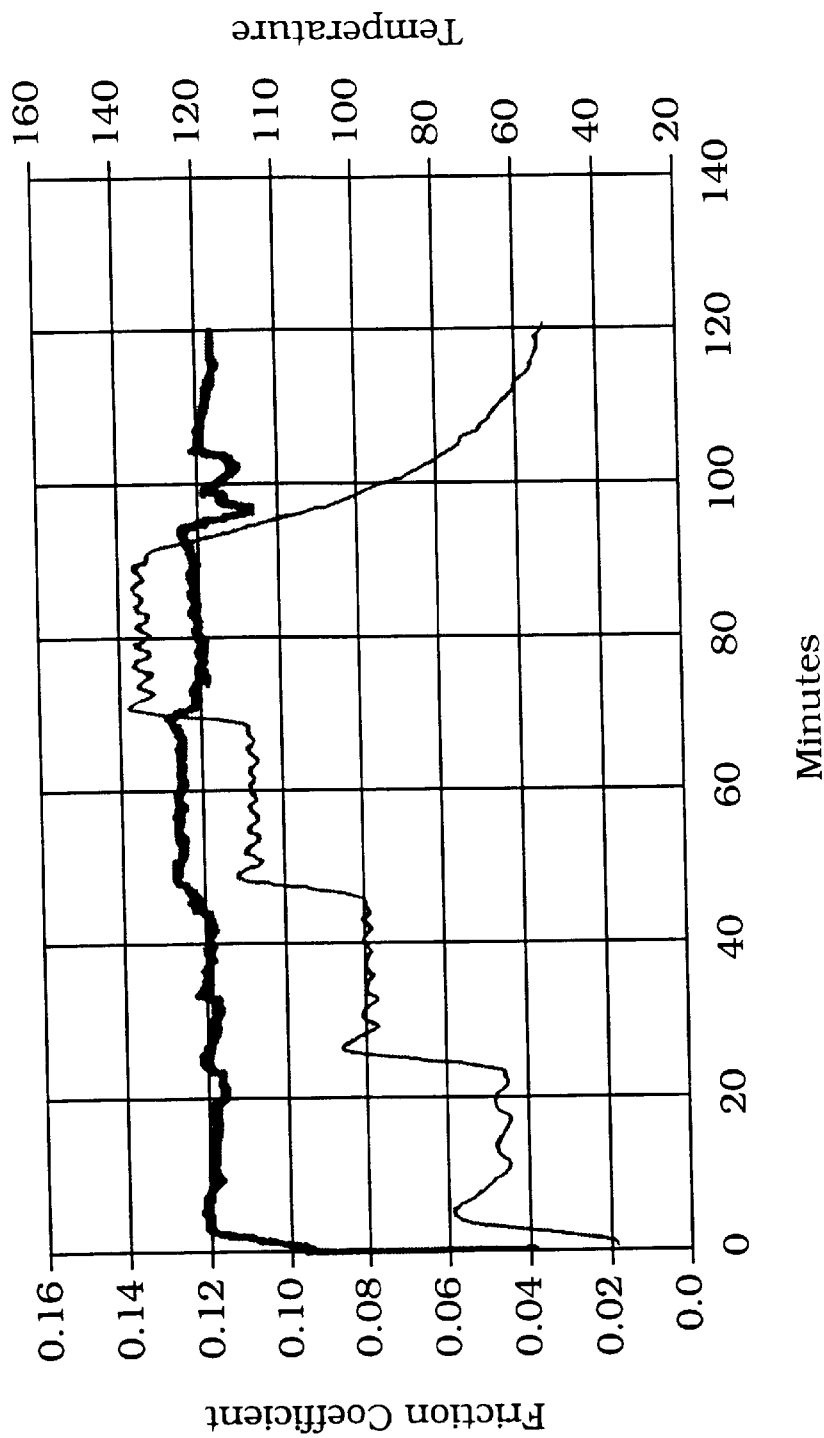
FIG. 1 shows the results of frictional performance measurements (heavy trace) of an oil containing a commercial dinuclear molybdenum additive over time. The oil's temperature was varied during the test, temperature is depicted in the fine trace.

The present invention is a composition capable of improving the friction reduction properties of a used lubricating oil. The friction reduction properties of a used oil can be enhanced or restored by adding to a major amount of used oil of lubricating viscosity a minor amount of at least one trinuclear molybdenum compound preferably having the formulas $Mo_3S_7(dtc)_4$, $Mo_3S_4(dtc)_4$, and mixture thereof wherein dtc represents diorganodithiocarbamate ligands and mixtures thereof having a sufficient number of carbon atoms among all the ligands' organo groups to render the compound soluble or dispersible in a lubricating oil.

In another embodiment, a minor amount of at least one trinuclear molybdenum compound is added to a fresh oil in order to enhance its effectiveness, particularly its friction reducing and wear reducing effectiveness.

DETAILED DESCRIPTION OF THE INVENTION

The lubricating oil compositions of the present invention include a major amount of oil of lubricating viscosity. This oil may be selected from vegetable, animal, mineral, or synthetic oils. The oils may range in viscosity from light distillate mineral oils to heavy lubricating oils such as gas engine oil, mineral lubricating oil, motor vehicle oil, and heavy duty diesel oil. A used lubricating oil is one that has been subjected to operating conditions such as to exposure to high shear forces, exposure to high temperature, exposure to a hostile chemical or physical environment, or similar conditions. The compounds of the present invention can also be used as additives in the formulation of fresh lubricating oil compositions. As such they possess superior friction reducing properties compared with dinuclear molybdenum sulfide additives that are known in the art. In cases where the compounds of the present invention are added to a used lubricating oil that was formulated using additives that are known in the art, the resulting friction reducing performance may exceed that of the originally formulated fresh oil.

In general, the viscosity of the oil will range from about 2 centistokes to about 30 centistokes and especially in the range of 5 centistokes to 20 centistokes at 100° C. The oils may be unrefined, refined, and re-refined.

The lubricant compositions of the present invention include a minor amount of a compound selected from trinuclear molybdenum compounds, preferably those having the formula $Mo_3S_7(dtc)_4$ and $Mo_3S_4(dtc)_4$ and mixtures thereof, wherein dtc represents diorganodithiocarbamate ligands and mixtures thereof that are independently selected, preferably monoanionic, ligands. Desirably, these ligands have hydrocarbyl organo groups and should have organo groups with a sufficient number of carbon atoms to render the compound soluble or dispersible in the oil. Generally at least 21 carbon atoms should be present among all of the organo groups of the compound's ligands.

The term "hydrocarbyl" denotes a substituent having carbon atoms directly attached to the remainder of the ligand and is predominantly hydrocarbyl in character within the context of this invention. Such substituents include the following:

1. Hydrocarbon substituents, that is, aliphatic (for example alkyl or alkenyl), alicyclic (for example cycloalkyl or cycloalkenyl) substituents, aromatic-, aliphatic- and alicyclic-substituted aromatic nuclei and the like, as well as cyclic substituents wherein the ring is completed through another portion of the molecule (that is, any two indicated substituents may together form an alicyclic group).

2. Substituted hydrocarbon substituents, that is, those containing non-hydrocarbon groups which, in the context of this invention, do not alter the predominantly hydrocarbyl character of the substituent. Those skilled in the art will be aware of suitable groups (e.g., halo, (especially chloro and fluoro), amino, alkoxyl, mercapto, alkylmercapto, nitro, nitroso, sulfoxy, etc.)

3. Hetero substituents, that is, substituents which, while predominantly hydrocarbon in character within the context of this invention, contain atoms other than carbon present in a chain or ring otherwise composed of carbon atoms.

Importantly, the organo groups of the ligands have a sufficient number of carbon atoms to render the compound soluble or dispersible in the oil. For example, the number of carbon atoms in each group will generally range between about 1 to about 100, preferably from about 1 to about 30, and more preferably between about 4 to about 20. Preferred ligands include dialkyldithiophosphate, alkylxanthate, and dialkyldithiocarbamate, and of these dialkyldithiocarbamate is more preferred. Organic ligands containing two or more of the above functionalities are also capable of serving as ligands and binding to one or more of the cores. Those skilled in the art will realize that formation of the compounds of the present invention requires selection of ligands having the appropriate charge to balance the core's charge. Two or more trinuclear cores interconnected by means of one or more ligands are within the scope of the invention. Also within the scope of the invention are structures wherein oxygen and/or selenium are substituted for sulfur in the cores.

Compounds with the formula $Mo_3S_7(dtc)_4$ are represented by a trinuclear molybdenum-sulfur core having the structure

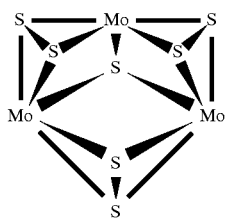

and ligands having the structure

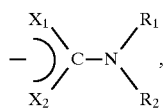

wherein $X_1$ and $X_2$ are independently selected from the group of oxygen and sulfur and $R_1$ and $R_2$ are H and organo groups that may be the same or different and are preferably the same and are selected from alkyl, aryl, substituted aryl, and ether groups. Importantly, the total number of carbon atoms present among all the compound's ligand's organo groups should be sufficient to render the compound soluble or dispersible in oil. For example, the number of carbon atoms in each hydrocarbyl or organo group will preferably range from 1 to 30, and more preferably from 4 to 20. These compounds are referred to as trinuclear molybdenum sulfide compounds.

Compounds with the formula $Mo_3S_4(dtc)_4$ are represented by a trinulcear molybdenum-sulfur core having the structure

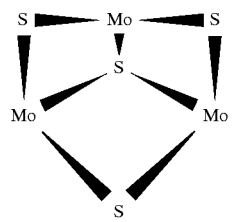

and ligands having the structure

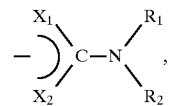

wherein $X_1$ and $X_2$ are independently selected from the group of oxygen and sulfur and $R_1$ and $R_2$ are H, or organo groups that are preferably hydrocarbyl groups that may be the same or different and are preferably the same, and are selected from alkyl, aryl, substituted aryl, and ether groups. Importantly, the total number of carbon atoms present among all the organo groups of the compound's ligands should be sufficient to render the compound soluble or dispersible in oil. For example, the number of carbon atoms in each organo and hydrocarbyl group will preferably range from 1 to 30, and more preferably from 4 to 20. These compounds are referred to as trinuclear molybdenum sulfide compounds.

Without wishing to be bound by any theory it is believed that two or more trinuclear cores may be bound or interconnected by means of one or more ligands, and the ligands may be multidentate. Such structures fall within the scope of this invention. This includes the case of a multidentate ligand having multiple connection to a single core.

Oil-soluble or dispersible trinuclear molybdenum compounds can be prepared by reacting in the appropriate liquid(s)/solvent(s) $(NH_4)_2Mo_3S_{13} \cdot n(H_2O)$, where n varies between 0 and 2 and includes non-stoichiometric values, with a suitable ligand source such as a tetralkylthiuram disulfide. Other oil-soluble or dispersible trinuclear molybdenum compounds can be formed during a reaction in the appropriate solvent(s) of $(NH_4)_2Mo_3S_{13} \cdot n(H_2O)$, a ligand source such as tetralkylthiuram disulfide, dialkyldithiocarbamate, or dialkyldithiophosphate, and a sulfur abstracting agent such as cyanide ions, sulfite ions, or substituted phosphines. Alternatively, a trinuclear molybdenum-sulfur halide salt such as $[M']_2[Mo_3S_7A_6]$, where M' is a counter ion, and A is a halogen such as Cl, Br, or I, may be reacted with a ligand source such as a dialkyldithiocarbamate in the appropriate liquid(s)/solvent(s) to form an oil-soluble or dispersible trinuclear molybdenum compound. Suitable liquid(s)/solvent(s) include for example aqueous and organic liquid(s)/solent(s).

In general, the compounds prepared as outlined above can be purified by well known techniques such as chromatography and the like; however, it may not be necessary to purify the compounds. Crude mixtures that contain substantial amounts of the compound have been found to be effective.

A compound's oil solubility or dispersibility may be influenced by the number of carbon atoms in the ligands' organo groups. In the compounds of the present invention, at least 21 total carbon atoms should be present among all the ligands' organo groups. Preferably, the ligand source chosen has a sufficient number of carbon atoms in its organo groups to render the compound soluble or dispersible in the lubricating composition.

The terms "oil-soluble" or "dispersible" used herein do not necessarily indicate that the compounds or additives are soluble, dissolvable, miscible, or capable of being suspended in the oil in all proportions. These do mean, however, that they are, for instance, soluble or stably dispersible in oil to an extent sufficient to exert their intended effect in the environment in which the oil is employed. Moreover, the additional incorporation of other additives may also permit incorporation of higher levels of a particular additive, if desired.

The lubricating compositions contain ligand-bearing, trinuclear, molybdenum sulfur compounds in minor effective amounts of preferably from 1 ppm to 2,000 ppm by weight molybdenum from the trinuclear molybdenum compound, more preferably from 5 to 750 ppm, and most preferably from 10 to 300 ppm, all based on the weight of the lubricating composition.

Concentrates of the compounds of the present invention in a suitable oleagenous carrier provide a convenient means of handling the compounds before their use. Oils of lubricating viscosity, such as those described above, as well as aliphatic, naphthenic, and aromatic hydrocarbons are examples of suitable oleagenous carrier fluids. These concentrates may contain about 1 to about 90 weight percent of the compound based on the weight of carrier, although it is preferred to maintain the compound's concentration between about 20 and 70 weight percent.

It is believed that the fuel economy performance of a vehicle powered by an internal composition engine is related to the friction reducing properties of the lubricating oil composition used in the engine. Consequently, it is expected that compounds that restore the friction reducing properties of a used oil would also restore the fuel economy performance of a vehicle having an engine with such a used oil. One embodiment of the invention, therefore, is a method for improving the fuel economy performance of an engine such as an internal combustion engine wherein the engine is lubricated by a used lubricating oil whose friction reduction performance has decreased from an earlier higher value.

In still another embodiment, the compounds of the present invention are added to a lubricating composition that did not exhibit sufficient friction reduction performance even when freshly formulated. In this embodiment the composition can be added to a used or fresh oil in order to improve the friction reduction performance of the composition beyond its initial value when fresh.

In these embodiments, the compositions of the present invention can be added to the engine's used oil as a concentrate between oil changes in order to restore fuel economy to at least its original value.

Other known lubricant additives may be compatible with the invention and can be used for blending in the lubricant composition of this invention. These include for example friction-reducing agents, dispersants, single or mixed metal detergents, pourpoint depressants, viscosity improvers, antioxidants, surfactants, and antiwear agents. These can be combined in proportions known in the art. For example, beneficial lubricant additives containing phosphorus and/or sulfur compounds such as ZDDP may be prepared and used with the compounds of the present invention. However, the compounds of the present invention may be effective or may even possess improved properties when used in lubricating compositions that are free or substantially free of phosphorous and/or sulfur except for the phosphorous or sulfur contained in the trinuclear molybdenum compounds of the present invention. A lubricating composition that is substantially free of phosphorous and/or sulfur is one in which the amount of phosphorous and/or sulfur is no more than is inherently present in oils of lubricating viscosity.

The lubricating composition and concentrates of the present invention comprise defined components that may or may not remain the same chemically before and after mixing with an oleagenous carrier. This invention encompasses compositions and concentrates which comprise the defined components before mixing or after mixing, or both before and after mixing.

The invention will be more fully understood by reference to the following examples illustrating various modifications of the invention which should not be construed as limiting the scope thereof.

EXAMPLE 1

In order to test the effectiveness of friction reduction by the addition of molybdenum containing compounds to used engine lubricants, a dimeric molybdenum additive $(Mo_2O_2S_2(dtc)_2)$, and several novel trimeric molybdenum compounds $Mo_3S_4((2ethylhexyl)_2dtc)_4$ and $Mo_3S_7((coco)_2dtc)_4$ were added at a concentration of 500 ppm molybdenum to a non-molybdenum containing oil which was aged in a Honda generator engine for 72 hours under conditions which simulate a Sequence IIIE engine test.

As used herein "coco" is an alkyl chain or mixtures of chains of varying even numbers of carbon atoms of from about typically $C_8$ to $C_{18}$.

Aging was conducted in a 2 cylinder, carburated, four stroke, water-cooled, 12 horsepower, Honda "generator engine". The engine was attached to a 6.5 kw electric generator during the test.

The engine was operated under steady state conditions at 3,600 rpm, a sump temperature of 150° C., an air/fuel ratio of 16.5/1 and a fixed power output of 4.8 kw.

The frictional performance of the aged oil treated with the various molybdenum additives was determined using a Cameron-Plint TE77 tribometer. The test protocol used a 6 mm. steel ball in reciprocating motion against a flat steel plate under a normal load of 5 kg., a stroke length of 7 mm., and a reciprocation frequency of 22 Hz. During the test the oil is held for approximately 20 minutes at each of four temperatures 50°, 80°, 110°, and 135° C. while the friction coefficient is measured.

Figure 2:
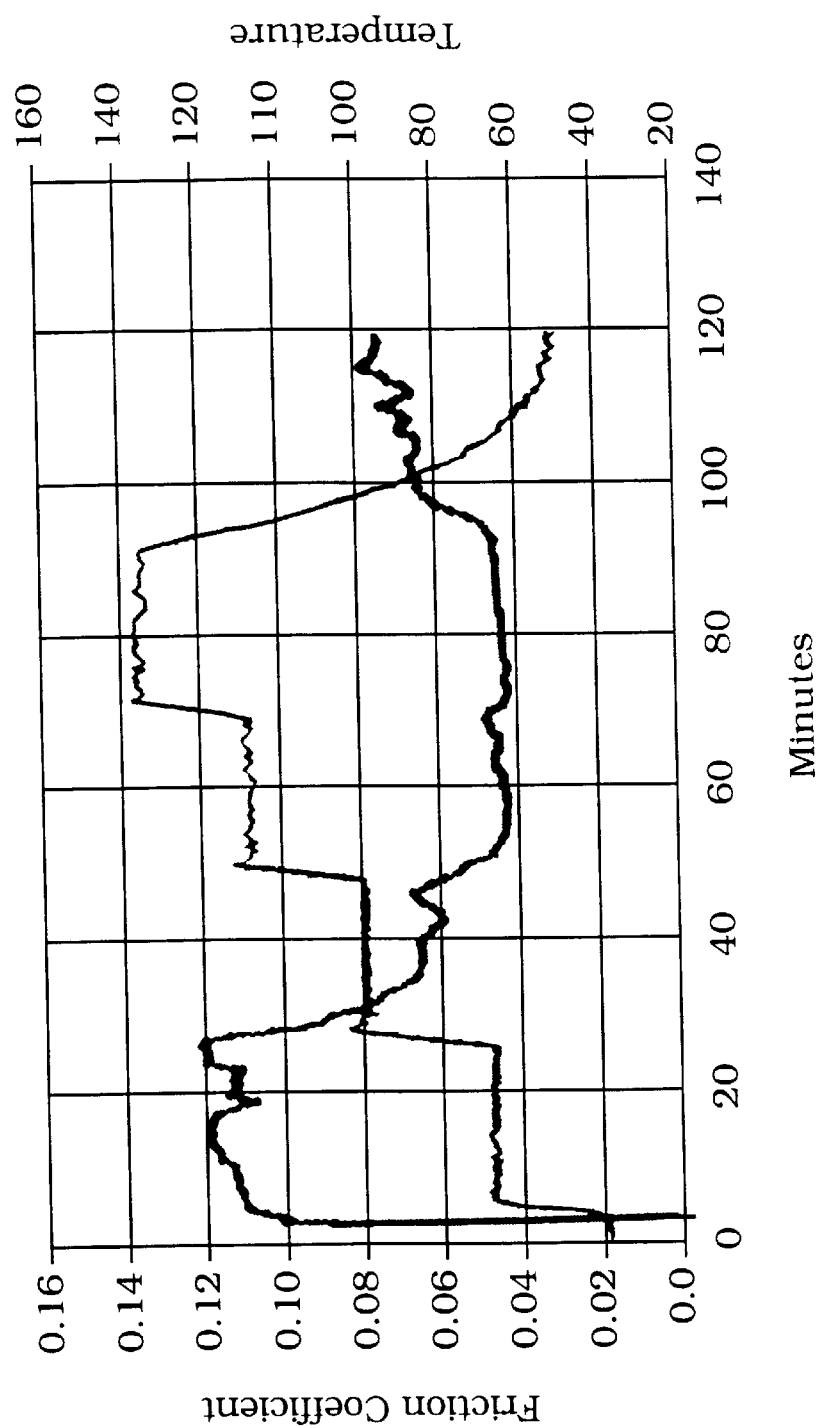
FIG. 2 shows the results of frictional performance measurements (heavy trace) of an oil containing a compound having the formula $Mo_3S_4((2\text{-ethylhexyl})_2dtc_2)_4$. The oil's temperature was varied during the test; temperature is depicted in the fine trace.
Figure 3:
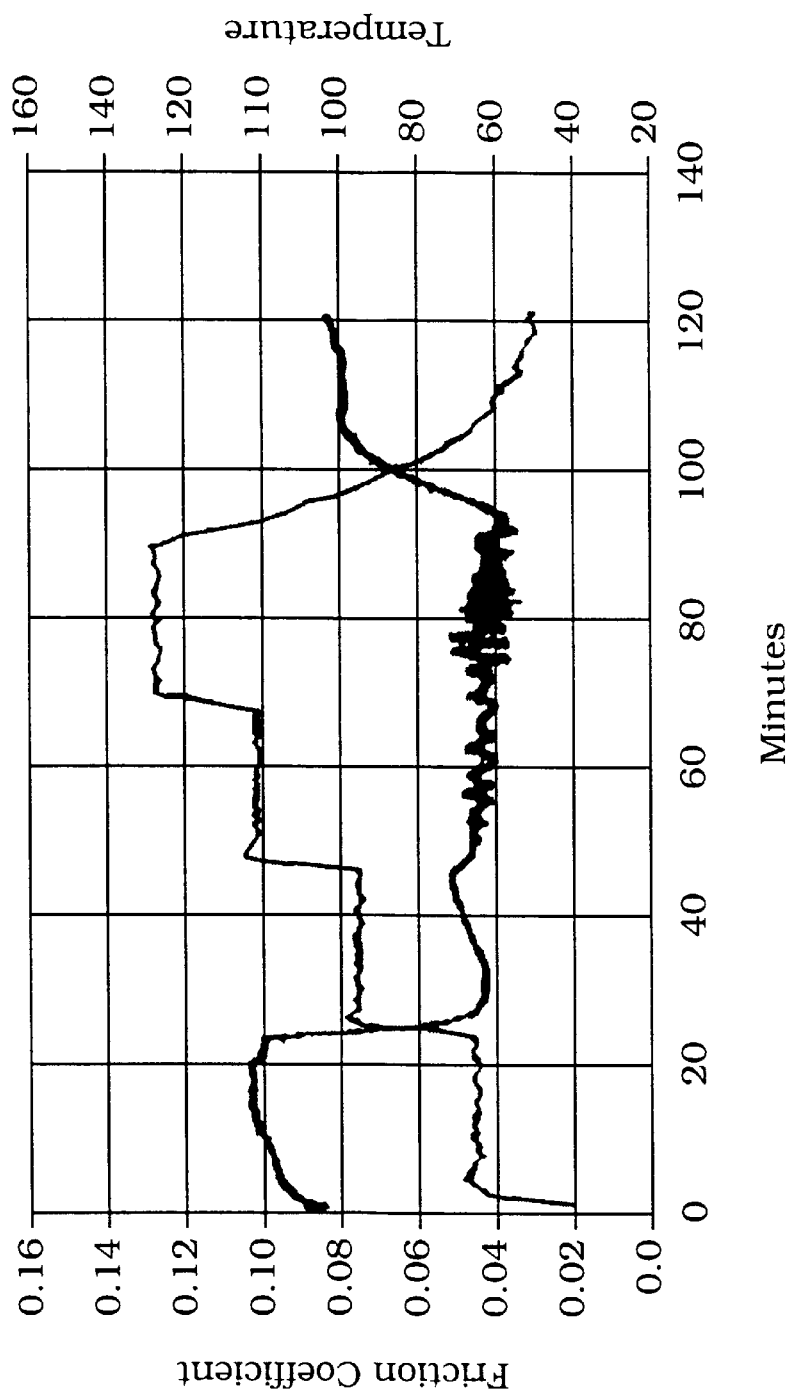
FIG. 3 shows the results of frictional performance measurements (heavy trace) of an oil containing a compound having the formula $Mo_3S_7((coco)_2dtc)_4$. The oil's temperature was varied during the test; temperature is depicted in the fine trace.

From the friction trace in FIG. 1, it may be clearly seen that the commercial dinuclear molybdenum additive $Mo_2O_2S_2(dtc)_2$ does not impart the expected low friction coefficients, generally <0.06 at temperatures over 100° C. for a fully effective molybdenum additive, to the oil. On the other hand, FIGS. 2 and 3 show that the trinuclear molybdenum compounds complexes, $Mo_3S_4((Z-ethylhexyl)_2dtc)_4$ and (FIG. 2) $Mo_3S_7((coco)_2dtc)_4$, (FIG. 3) give very low friction coefficients between 0.04 and 0.05 at the higher test temperatures.

COMPARATIVE EXAMPLE

The friction reducing properties of commercial dinuclear molybdenum additives were also investigated for comparison with the compounds in the present invention. Fresh oil of lubricating viscosity was used in an internal combustion engine under operating conditions for various times to form a used lubricating oil. A dinuclear molybdenum additive having the formual $Mo_2O_2S_2(dtc)_2$ was then combined with the used lubricating oil at 500 ppm Mo. The frictional performance of the additive was then determined according to the method of Example 1.

Figure 4:
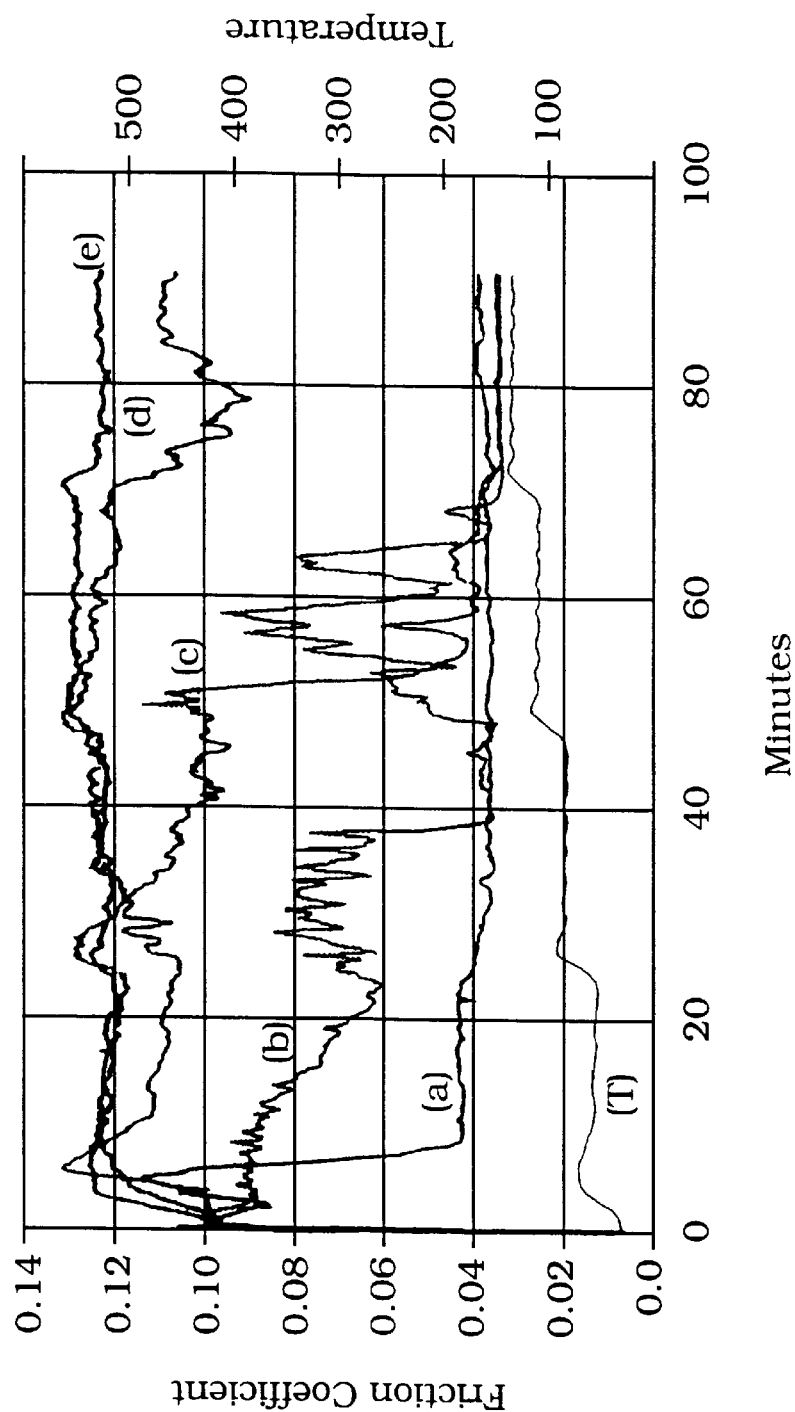
FIG. 4 shows the frictional performance of 5 lubricating compositions. Prior to the start of the measurement, four samples of lubricating oil were aged for a period of time under operating conditions. One sample was not aged. At the conclusion of aging, a commercial dinuclear molybdenum compound was added to the oil. The temperatures of each admixture were varied in time (trace T), and frictional performance was measured for the oil that was not aged (trace a), aged 12 hours (trace b), aged 23 hours (trace c), aged 36 hours (trace d), and aged 72 hours (trace e).

FIG. 4 shows the results of those tests. The different traces show the performance of mixtures of the dinuclear molybdenum additive with lubricating oils aged for progressively longer times. Trace (a) is a fresh oil, trace (b) is aged 12 hours, trace (c) is aged 23 hours, trace (d) is 36 hours, and trace (e) is aged 72 hours. Trace (T) shows the variation of temperature with time during the performance test.

FIG. 4 reveals that while some improvement in friction reducing performance is obtained when the dinuclear molybdenum additive is combined with a fresh oil, that benefit gradually diminishes when that additive is combined with lubricating oils that have been aged under operating conditions. In these examples, no benefit is obtained when the commercial additive is combined with oils that have aged 72 hours or longer. By comparison, Example 1 shows that a benefit is obtained when combining lubricating oils that have been aged for 72 hours with the trinuclear molybdenum compounds of the present invention.

Comparative Example

The friction reducing properties of commercial dinuclear molybdenum additives were also investigated for comparison with the compounds in the present invention. Fresh oil of lubricating viscosity was used in an internal combustion engine under operating conditions for various times to form a used lubricating oil. A dinuclear molybdenum additive having the formula $Mo_2O_2S_2(dtc)_2$ was then combined with the used lubricating oil. The frictional performance of the additive was then determined according to the method of Example 1.

FIG. 4 shows the results of those tests. The different traces show the performance of mixtures of the dinuclear molybdenum additive with lubricating oils aged for progressively longer times. Trace (a) is a fresh oil, trace (b) is aged 12 hours, trace (c) is aged 23 hours, trace (d) is 36 hours, and trace (e) is aged 72 hours. Trace (T) shows the variation of temperature with time during the performance test.

The FIG. 4 reveals that while some improvement in friction reducing performance is obtained when the dinuclear molybdenum additive is combined with a fresh oil, that benefit gradually diminishes when that additive is combined with lubricating oils that have been aged under operating conditions. In these examples, no benefit is obtained when the commercial additive is combined with oils that have aged 72 hours or longer. By comparison, Example 1 shows that a benefit is obtained when combining lubricating oils that have been aged for 72 hours with the trinuclear molybdenum compounds of the present invention.

What is claimed is:

1. A method for improving the friction reduction performance of a lubricating oil comprising adding to the lubricating oil an oil-soluble or dispersible molybdenum sulfur compound having a trinuclear core consisting of molybdenum and sulfur atoms, the core having at least one ligand selected from the group consisting of diorganodithiocarbamate, alkylxanthate, and dialkyldithiophosphate.

2. The method of claim 1 wherein the trinuclear molybdenum sulfur compound is selected from compounds having the formulas $Mo_3S_7(dtc)_4$, $Mo_3S_4(dtc)_4$, and mixtures thereof, wherein dtc represents independently selected dialkyldithiocarbamate ligands.

3. The method of claim 1 wherein the oil is a used oil.

4. The method of claim 1 wherein the compound comprises cores selected from the group consisting of

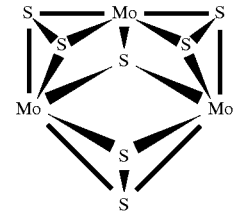

and

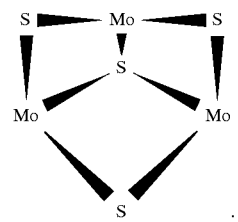

5. The method of claim 1 wherein the compounds contain ligands having the structure

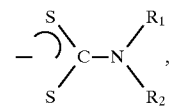

wherein $R_1$ and $R_2$ are independently selected from the group of hydrogen, and organo groups.

6. The method of claim 5 wherein the compound's concentration by weight in the oil ranges from about 50 ppm to about 50,000 ppm based on the weight of lubricating oil.

7. The method of claim 5 wherein the total number of carbon atoms among all the ligands' organo groups is at least 21.

8. The method of claim 5 wherein the organo groups are alkyl groups and the number of carbon atoms in each alkyl group ranges from about 1 to 30.

9. The method of claim 8 wherein the number of carbon atoms in each alkyl group ranges from about 4 to about 20.

10. A concentrate for blending with a lubricating oil in order to improve the lubricating oils friction reducing properties comprising an oleagenous carrier fluid and from about 1 to about 90 weight percent of a compound, based on the weight of the carrier and compound, the compound selected from the group of compounds having the formulas $Mo_3S_7(dtc)_4$, $Mo_3S_4(dtc)_4$, and mixtures thereof, wherein dtc represents independently selected diorganodithiocarbamate ligands containing independently selected organo groups and wherein the ligands have a sufficient number of carbon atoms among all the ligands' organo groups to render the compound soluble or dispersible in the lubricating oil.

11. The additive concentrate of claim 10 wherein the oleagenous carrier is selected from base stock, animal oils mineral oils, vegetable oils and synthetic oils.

* * * * *